United States Patent
Lai

(10) Patent No.: US 7,338,811 B2
(45) Date of Patent: Mar. 4, 2008

(54) INTEGRATED CIRCUIT CHIP FOR BIOASSAYS

(75) Inventor: Derhsing Lai, Yardley, PA (US)

(73) Assignee: Vincogen Corporation, North Brunswick, NJ (US)

( * ) Notice: Subject to any disclaimer, the term of this patent is extended or adjusted under 35 U.S.C. 154(b) by 574 days.

(21) Appl. No.: 10/396,269

(22) Filed: Mar. 25, 2003

(65) Prior Publication Data

US 2004/0029109 A1 Feb. 12, 2004

Related U.S. Application Data

(60) Provisional application No. 60/367,699, filed on Mar. 26, 2002.

(51) Int. Cl.
| | |
|---|---|
| G01N 15/06 | (2006.01) |
| G01N 21/00 | (2006.01) |
| G01N 25/18 | (2006.01) |
| G01N 33/53 | (2006.01) |
| G01N 33/553 | (2006.01) |
| G01N 33/566 | (2006.01) |
| B01L 3/00 | (2006.01) |
| B32B 5/02 | (2006.01) |
| C12Q 1/00 | (2006.01) |
| C12Q 1/68 | (2006.01) |
| C12M 3/00 | (2006.01) |
| C12M 1/34 | (2006.01) |

(52) U.S. Cl. ............... 436/525; 422/55; 422/57; 422/61; 422/68.1; 422/82.01; 422/98; 435/4; 435/6; 435/7.1; 435/287.1; 435/287.2; 435/287.9; 436/501; 436/518; 436/524; 436/149; 436/150; 436/151

(58) Field of Classification Search ........... 422/55, 422/57, 61, 68.1, 82.01, 98; 435/4, 6, 7.1, 435/287.1, 287.9, 287.2; 436/501, 518, 524, 436/525, 149, 150, 151
See application file for complete search history.

(56) References Cited

U.S. PATENT DOCUMENTS

| | | | |
|---|---|---|---|
| 5,736,332 | A | 4/1998 | Mandecki |
| 5,741,462 | A | 4/1998 | Nova et al. |
| 5,751,629 | A | 5/1998 | Nova et al. |
| 5,772,966 | A | 6/1998 | Maracas et al. |
| 5,874,214 | A | 2/1999 | Nova et al. |
| 5,981,166 | A | 11/1999 | Mandecki |
| 6,001,571 | A | 12/1999 | Mandecki |

(Continued)

FOREIGN PATENT DOCUMENTS

WO WO9719958 6/1997

(Continued)

OTHER PUBLICATIONS http://www.pharmaseq.com/illustration.html, no date available.

(Continued)

*Primary Examiner*—Long V. Le
*Assistant Examiner*—Jacqueline A. DiRamio
(74) *Attorney, Agent, or Firm*—Cheryl H. Agris

(57) ABSTRACT

The invention is directed to novel IC chips containing substances used particularly in bioassays. Furthermore, the invention is directed to assay methods and kits using these chips.

60 Claims, 12 Drawing Sheets

U.S. PATENT DOCUMENTS

| | | |
|---|---|---|
| 6,025,129 A | 2/2000 | Nova et al. |
| 6,051,377 A | 4/2000 | Mandecki |
| 6,087,186 A | 7/2000 | Cargill et al. |
| 6,136,274 A | 10/2000 | Nova et al. |
| 6,225,625 B1 | 5/2001 | Pirrung et al. |
| 6,284,459 B1 | 9/2001 | Nova et al. |
| 6,319,668 B1 | 11/2001 | Nova et al. |
| 6,329,139 B1 | 12/2001 | Nova et al. |
| 6,331,273 B1 | 12/2001 | Nova et al. |
| 6,340,588 B1 | 1/2002 | Nova et al. |
| 6,352,854 B1 | 3/2002 | Nova et al. |
| 6,361,950 B1 | 3/2002 | Mandecki |
| 6,372,428 B1 | 4/2002 | Nova et al. |
| 6,376,187 B1 | 4/2002 | Mandecki |
| 6,387,623 B1 | 5/2002 | Mandecki |
| 6,416,714 B1 | 7/2002 | Nova et al. |
| 6,417,010 B1 | 7/2002 | Cargill et al. |
| 6,725,316 B1* | 4/2004 | Gans ................ 710/307 |
| 2002/0006673 A1 | 1/2002 | Mandecki |
| 2003/0143619 A1* | 7/2003 | Mandecki ............ 435/6 |
| 2004/0096991 A1* | 5/2004 | Zhang ............... 436/518 |

FOREIGN PATENT DOCUMENTS

| | | |
|---|---|---|
| WO | WO9720073 | 6/1997 |
| WO | WO9720074 | 6/1997 |

OTHER PUBLICATIONS

Service, 1995, Science 270:577.

Moran et al., 1995, J. Amer. Chem. Soc. 277: 10787-10788.

* cited by examiner

Bit0= 0 or 1
Bit1= 0 or 1
Bit2= 0 or 1
Bit3= 0 or 1
Bit4= 0 or 1

US 7,338,811 B2

INTEGRATED CIRCUIT CHIP FOR BIOASSAYS

PRIORITY CLAIM

This application claims the benefit of U.S. Provisional Application No. 60/367,699, filed Mar. 26, 2002, the contents of which are incorporated herein by reference.

FIELD OF THE INVENTION

The invention is directed to novel IC chips containing substances used particularly in bioassays. The invention is directed to a novel use of an integrated circuit chip comprising a transponder encoded with information that is transmitted to a receiver in response to a radio signal in assaying a biological molecule. Furthermore, the invention is directed to assay methods and kits using these chips.

BACKGROUND OF THE INVENTION

Solid-Phase Assay Procedures

Solid phase assays have been used to determine the presence and/or amount of substances such as proteins, peptides, carbohydrates, lipids and small molecules in a variety of biological samples (e.g., blood, serum, urine, saliva, tissue homogenates). The solid phase is used to separate molecules that bind to the solid phase from those that do not. Small beads are generally used as the solid phase to capture the analyte. However, in conventional procedures, it is difficult to perform a multiplicity of assays in a single sample at about the same time (multiplex assay).

One approach that has been taken in order to increase the scope of the multiplex assay is to use transponders associated with the solid phase beads to index the particles constituting the solid phase (see, for example, U.S. Pat. No. 5,641,634, WO 97/20074). A diagrammatic representation of the system for use in detecting DNA sequences is disclosed is shown at pharmaseq.com/illustration.html. The transponder has a photovoltaic cell as its power resource through light or laser (column 5, line 50-65; FIG. 6). A laser is used to activate the light cell and supply the power. The transponder then emits a radio signal. This can be a weakness.

Radiotags or transponders have also been used in combinatorial chemical approaches (reviewed in Service, 1995, Science 270:577). In one approach, a radiofrequency (RF) encodable microchip is coupled with a polypropylene capsule of derivatized polystyrene resin so that a radioscanner registers the identity of a capsule and the contents of each beaker it enters (see, U.S. Pat. Nos. 5,777,045 and 6,051,377 and Moran, et al., 1995, *J. Amer. Chem. Soc.* 117:10787-10788). The data is uploaded to a computer that keeps track of the order of addition to monomers to the capsule.

In another approach by Nova et al., the data obtained is actually stored on the microchip itself, using a transmitter that writes the information to the chip (see, for example, U.S. Pat. Nos. 5,741,462, 5,751,629, 5,874,214, 5,925,562 and 6,025,129). The data is not uploaded to the computer until the run is complete. Therefore the system disclosed comprises a recording device and storage unit. It has been suggested that this system may also be used in immunoassays and hybridization reactions and to detect macromolecules, to identify receptor bound ligands, and cell sorting.

RFID

A radio frequency identification system (RFID) carries information in suitable transponders that contain tags having information. The information on the tags is retrieved in response to a radio signal by machine-readable means (for a review of RFID, see www.aimglobal.org)

A basic RFID system contains the following three components:
(a) an antenna or coil
(b) a transponder programmed with unique information
(c) a receiver which decodes the unique information The antenna, which acts as a conduit between the transponder and receiver, emits radio signals to activate the tag on the transponder and read and write information to it.

The transponder contains a tag, which responds to a signal for the information it generated. It should be noted that the terms "transponder" and "tag" are used interchangeably in the art. The transponder or tag logic may be read-only or random access.

The receiver receives the information transmitted by the transponder and decodes it. The information may further be processed.

It has been suggested that RFID can be used in transportation and logistics, manufacturing and processing security, animal tagging, waste management, time and attendance, postal tracking airline baggage reconciliation and road toll management.

SUMMARY OF THE INVENTION

The invention is directed to an integrated circuit chip for use in an assay of a substance comprising:
(a) a transponder encoded with information which may include but is not limited to data or binary code which is transmitted to a receiver in response to a radio signal and
(b) at least one substance attached to said transponder.

In a specific embodiment, the chip of the present invention further comprises at least one metal option. As defined herein, a "metal option" is a wire that links circuits together and in a specific embodiment, connects to highest or lowest power. The invention is also directed to a method for obtaining said integrated circuit chip.

The invention is further directed to a system for assaying a substance comprising
(a) a radio frequency identification system comprising: (i) an antenna which emits a radio signal; (ii) a transponder having a read-only tag, wherein said tag contains unique information and said transponder activated by said antenna of (ii) and (iii) receiver which receives and decodes said information and
(b) at least one substance attached to said transponder.

In a specific embodiment, the system comprises (a) a radio frequency identification system comprising: (i) an antenna which emits a radio signal; (ii) a transponder having a read-only tag, wherein said tag contains binary code and said transponder activated by said antenna of (i) and (iii) receiver which receives and decodes said information and (b) at least one substance attached to said transponder.

In yet another specific embodiment, the chip of the present invention further comprises an electrode. The substance is attached to the chip so that it is contacted with the electrode. The substance may contain an electrochemiluminescent moiety.

The invention is further directed to methods for using said integrated circuit for detecting binding of a first substance to a second substance comprising (a) incubating the integrated chip of the present invention, said chip comprising a transponder and a first substance attached to said transponder with a second substance;

(b) analyzing the incubated mixture of step (a) to detect binding of said first substance and said second substance and (c) identifying the substance attached to said transponder.

The substance attached to said transponder may contain a detectable moiety; alternatively, the second substance may contain a detectable moiety. In yet another embodiment, a detectable moiety may be added to the incubated mixture of step (a). In an even further embodiment, the substance attached to the transponder is a biological substance.

In a specific embodiment, the invention is directed to a multiplex assay using the chips of the present invention comprising:

(a) providing multiple integrated circuit chips of the present invention;

(b) contacting said chips with one or more substances to determine if said substance binds to a substance on each of said chips;

(c) analyzing the incubated mixture of step (b) to detect binding of said substance to said chips and (d) identifying the biological molecules bound to said labeled substances In one more specific embodiment, the same substance is attached to each chip. In another more specific embodiment, a different substance is attached to each chip. In yet another embodiment, the substance is a biological sample. In yet another embodiment, the substance contains a detectable moiety. In yet a more specific embodiment, the method of the present invention may be used to detect a pathogen on a cell or diagnose a disease of disorder; create a patient profile, determine ingredients in herbs and/or for drug screening.

The invention is further directed to a kit for assaying a biological molecule comprising (a) a transponder comprising a tag with information which is transmitted to a receiver in response to a radio signal and (b) a detectable moiety and/or a substance library (e.g., phage display library, a DNA library, a natural products library).

The invention is further directed to a kit for assaying a biological molecule comprising (a) radiofrequency identification system comprising: (i) an antenna which emits a radio signal; (ii) a transponder having a read-only tag, wherein said tag contains unique information and said transponder activated by said antenna of (i) and (iii) receiver which receives and decodes said information and (b) a detectable moiety and/or substance library.

DETAILED DESCRIPTION OF THE INVENTION

Figure 1:
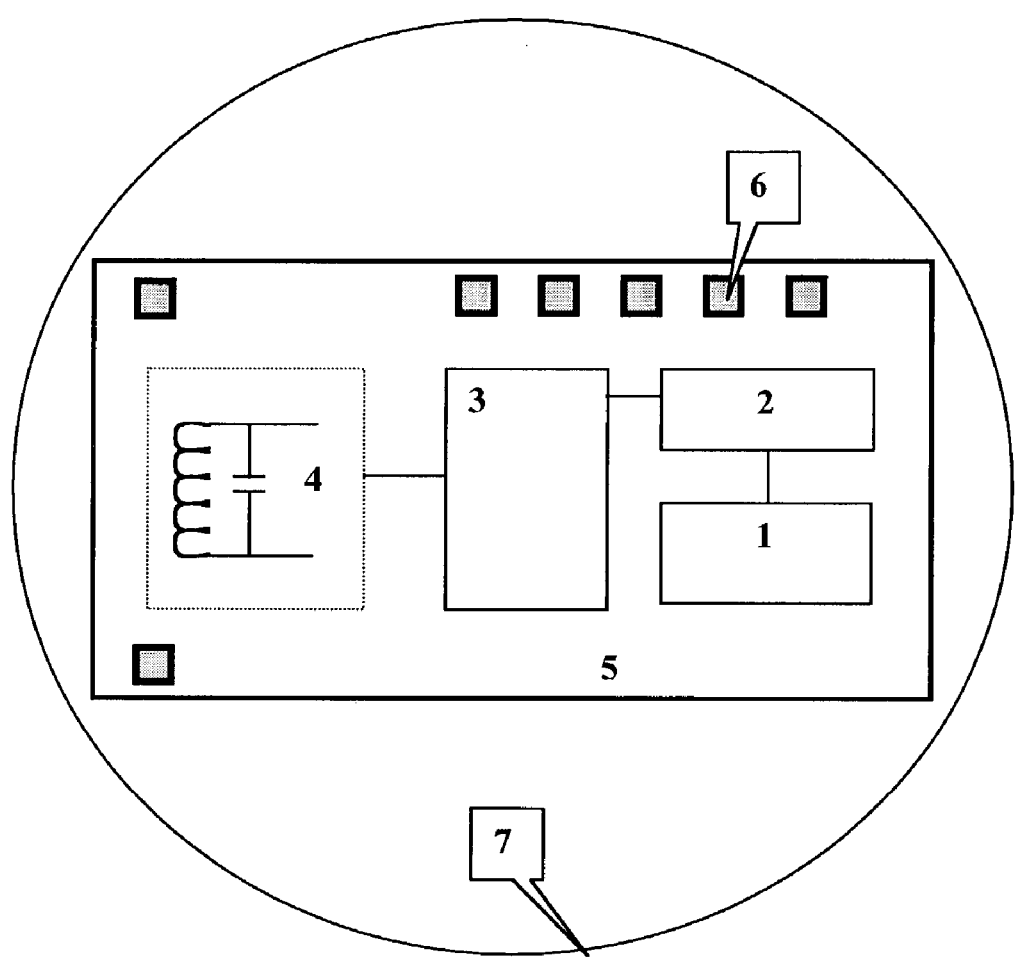
FIG. 1 shows a diagram of an RF ID system with "metal option".

The IC chip of the present invention contains a transponder and a substance attached to said transponder. The substance may be attached to the chip of the present invention using procedures known in the art.

In one embodiment, the substance is covalently attached to the chip using a conjugating agent known in the art. Such a conjugating agent includes but is not limited to aminoalkyl silanes [e.g. n-octadecyltrimethoxy-silane (OTMS); n-octadecyltrichlorosilane (OTCS)] [Kleinfeld et al (1988) Neurosci, 8, 4098-4120; Mooney et al, (1996) Proc. Natl. Acad. Sci. USA, 93, 12287-12291], aldehyde silanes, where aldehydes react with primary amines on the proteins to form a Schiff's base linkage [Macbeath et al., (2000) Science 289, 1760-1757]; albumin-alkyl absorption, [Hart et al, (1994) Electroanalysis 6, 617; Newman et al, (1992) Anal. Chim. Acta, 262, 13]; photoresist technology with methyl- and amino-terminated silanes [Britland et al (1992) Biotechnol. Progr, 8, 155-160; Britland et al, (1992) Exp. Cell Res. 198, 124-129]; nitroarylazide photochemistry with biotin-avidin [Pritchard et al, (1995) Anal. Chem., 67, 3605-3607; Hiller et al., (1987) Biochem. J. 248, 167]; perfluorophenylazide photochemistry with n-hydroxysuccinimide esters [Yan et al, (1994) Bioconjugate Chem., 5, 151-157]; diazirine photochemistry [Gao et al, (1995) Bioelectron 10, 317-328]; deep UV of silanes with EDA [Dulcey et al (1991) Science, 252, 551-554]; deep UV of silanes with OTS [Mooney et al., (1996) Proc. Natl. Acad. Sci, 93, 12287-12291]; alkane thios [Knoll et al., (1997) 34, 231-251] and laser vapor deposition [Morales et al., (1995) 10, 847-852].

One agent that can be used for non-specific, non-covalent attachment is poly-L-lysine. The target substance will be added to the poly-L-lysine treated or coated chip surface first. The non-specific, non-covalent bond will be formed between target substance and poly-L-lysine. This non-covalent bond will hold the target substance on the chip. This method can be used with various target substances, e.g. DNA, protein, and cell.

In another embodiment, the substance may be coated onto the chip. Specifically, the chip is directly incubated in a solution containing the substance. The chip is then transferred to the blocking solution (e.g. BSA or casein) [Vogt et al., (1987) J. Immunol. Methods 101, 43-50] to fill the uncovered space on the surface of chip. Non-covalent bonds will be formed between the substance and surface of the chips. The amount of the substance in the coating can be adjusted, depending on the request and the concentration of the substance in the solution.

All procedures are preferably for just one single substance. However, a mixture of several substances can be added to on the single chip for the primary screening purpose. The positive reaction of the primary screening chip can then be screened for each individual substance from this mixture in each single chip later.

The substance attached to the transponder may be a biological sample. In a particular embodiment, the biological sample is a cell, subcellular component, organelle or tissue. The biological sample could also be nucleic acid and/or protein isolated from cell, tissue, urine and saliva. In another embodiment, the substance attached to the transponder is a substance containing a non-radioactive detectable moiety, such as a whole cell, subcellular particle, virus, prion, viroid, lipid, fatty acid, nucleic acid, polysaccharide, protein, lipoprotein, lipopolysaccharide, glycoprotein, peptide, cellular metabolite, hormone, pharmacological agent, tranquilizer, barbiturate, alkaloid, steroid, vitamin, amino acid, sugar, non-biological polymer, synthetic organic molecule, organometallic molecule, inorganic molecule, biotin, avidin or streptavidin.

In a specific embodiment, members of a DNA or phage display library (e.g, T4 phage) may be attached to a plurality of transponders. The substance may also be an antibody; in a specific embodiment, the antibody is a monoclonal antibody. The substance may also be a receptor or a ligand. A ligand is a substance that binds to a receptor.

The substance may be labeled with a nonradioactive detectable moiety such as a chromophore, fluorophore or luminescent agent. An example of a chromogenic substrate is 5-bromo-4-chloro-3-indoyl phosphate.

Luminescence occurs when a molecule in an electronically excited state relaxes to a lower energy state by the emission of a photon. The luminescent agent in one embodiment may be a chemiluminescent agent. In chemiluminescence, the excited state is generated as a result of a chemical reaction, such as lumisol and isoluminol. In photoluminescence, such as fluorescence and phosphorescence, an electronically excited state is generated by the illumination of a molecule with an external light source. An example of bioluminescence is the enzyme, luciferase. In electrochemiluminescence (ECL), the electronically excited state is generated upon exposure of the molecule (or a precursor molecule) to electrochemical energy in an appropriate surrounding chemical environment. The general principle of ECL is described in Yang et al., 1994, Bio/Technology 12; 193-194. Examples of electrochemiluminescent agents are provided, for example, in U.S. Pat. No. 5,147,806, 5,641, 623 and U.S. application Ser. No. 2001/0018187 and include but are not limited to metal cation-liquid complexes, substituted or unsubstituted polyaromatic molecules, mixed systems such as aryl derivatives of isobenzofurans and indoles. The electrochemiluminescent chemical moiety may comprise, in a specific embodiment, a metal-containing organic compound wherein the metal is selected from the group consisting of ruthenium, osmium, rhenium, iridium, rhodium, platinum, palladium, molybdenum, technetium and tungsten.

In another embodiment, BIA technology may be used to detect the binding of a sample to the chip of the present invention. This technology uses surface plasmon resonance (SPR) technology [BIACORE AB, Sweden]. The principle of SPR has been described by Karlsson et al, (2000) 278, 1-13 and BIACORE AB [biacore.com/biomol/principle.shtml].

IC Chips

In one embodiment, the IC chip of the present invention is a component of an RFID system. Each transponder or tag is separately encoded with an index number to identify the substance attached to the IC chip. The chip may be a bead or rectangular in shape. The size may be in the range of about 200~1500 (μm) and is preferably about 1500 μm. In a specific embodiment, an antenna is attached to said transponder and the antenna may be linear or planar.

Figure 2:
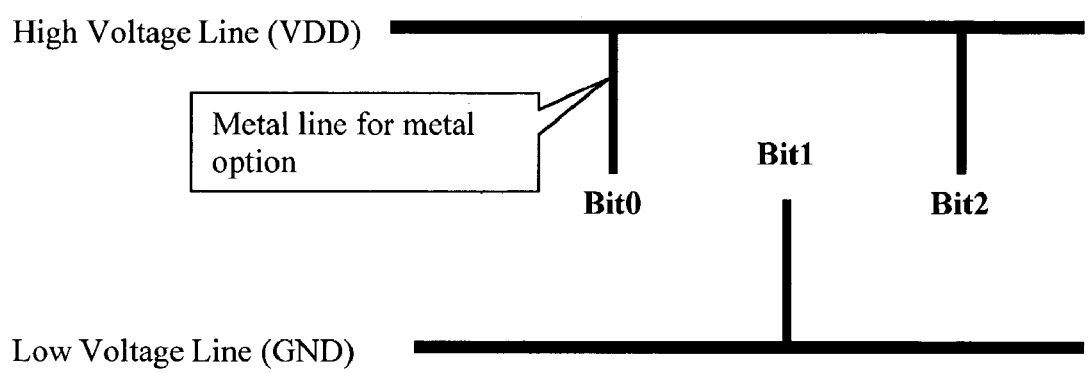
FIG. 2 shows a close up of a specific embodiment of the "metal option" component. Each metal line has two metal options, 0 or 1. Therefore, 14 Bits means fourteen metal options (0 or 1). The combination of all 14 metal lines series is $2^{14}$ ID.

The invention includes but is not limited to the following three IC chips:

(1) RF with "metal option" for ID without ECL application (see FIGS. 1 and 2). As defined herein, a "metal option" is a metal wire that connects to highest power (VDD) or lowest power (GND: ground). As a result, ROM, RAM and Flash are not needed. The metal option ID logic 1 creates an index ID by a metal photo mask process. A photomask is a special film for a semiconductor process. Modulator 2 converts the ID binary number to an RF band. The signal will transmit out to the air through the Analog Front End. The Capacitor and Oscillator will be inside those blocks. The Analog font end 3 is an up-converter circuit basically to up-convert the binary ID to high frequency. Antenna and Energy Gather Circuit 4 is for receiving and sending the radiofrequency energy in and out the chip. Internal Block 5 and Pins 6 for testing or other reserved function. The chip may optionally contain a layer 7. $SiO_2$ protects most of area of IC and only the pins areas 6 are exposed to air. It can be added by the IC manufacturer but is not necessary.

Figure 3:
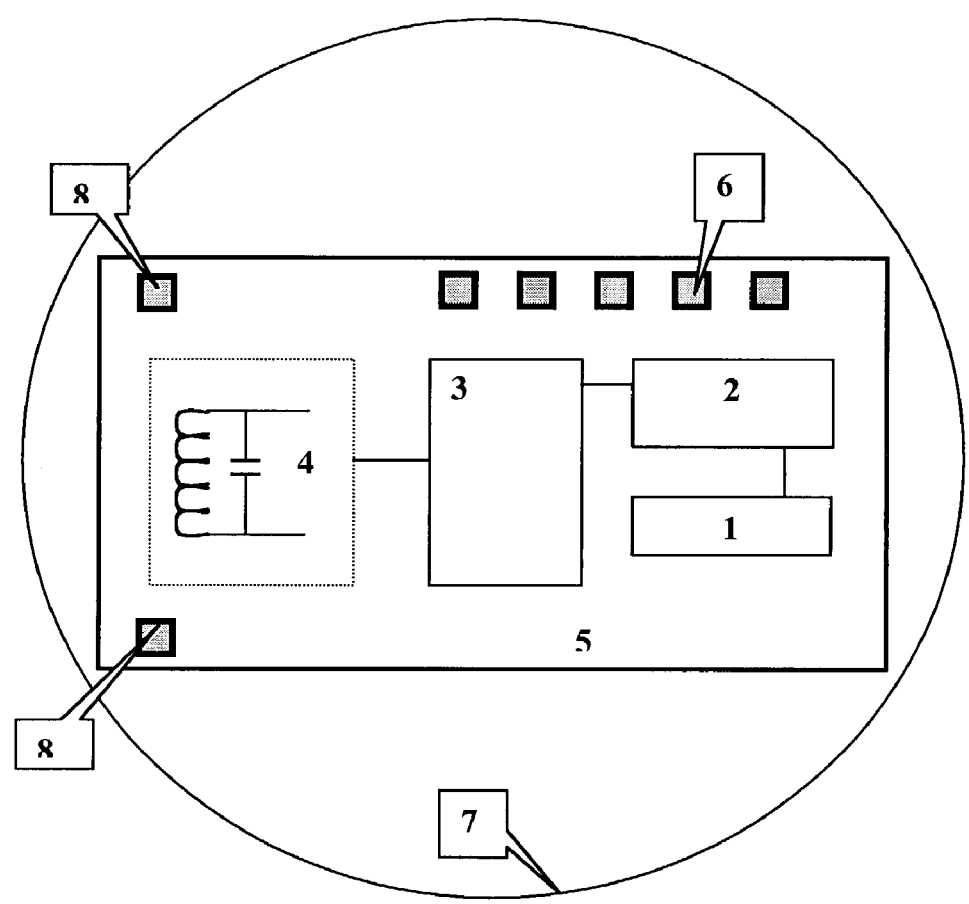
FIG. 3 shows RFID (metal option) with electrode for ECL.
Figure 4:
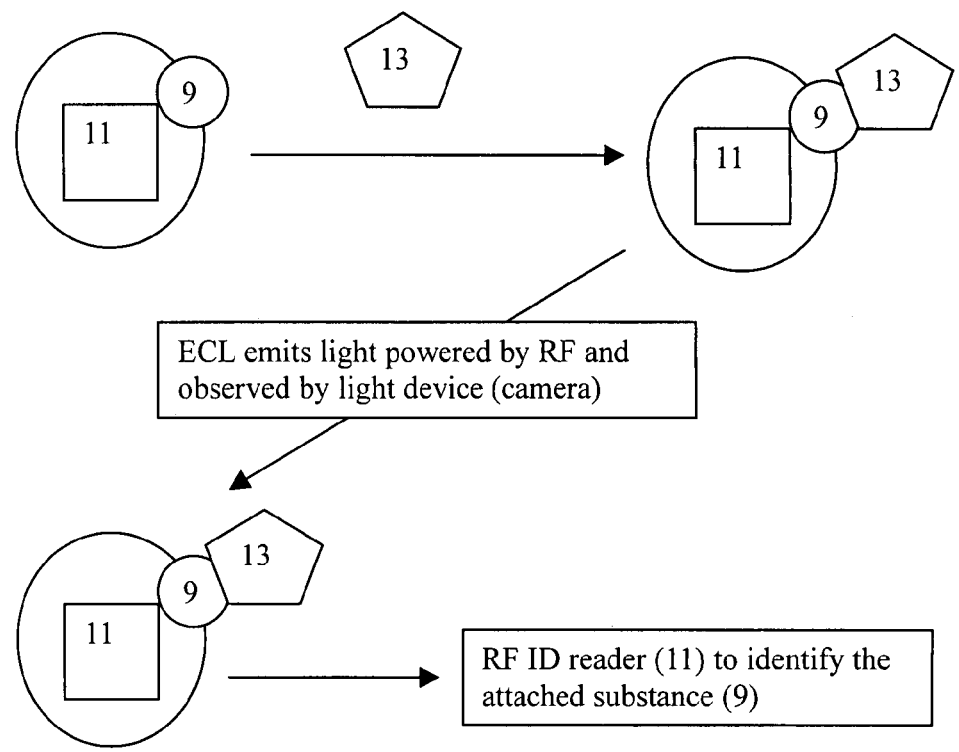
FIG. 4 depicts the procedure used with an ECL labeled substance 13 and RFID chip containing an electrode.

(2) RF with "metal option" for ID with ECL application (see FIGS. 3 and 4). As shown in FIG. 3, 1-7 are the same as above. This embodiment also comprises an electrode 8. Both metal option ID and electrode are on the same current and use the same electricity source. The substance has contact with the electrode 8 on the chip to let the ECL labeled substance bind. The electricity will pass through the ECL labeled substance and emit for example, the wavelength at 600-620 nm for ECL Ru substrate. Both RF ID and ECL signal can be detected at the same time. Alternatively, they can be detected separately that is ECL signal first, then RF ID with two inputs of radiofrequency. The IC chip of the present invention will use the electricity (~3V) generated by RF to power the ECL conjugated target 13 when it binds to the substance 9 to an electrode on said chip (see FIG. 4). This technology involves two components: the ECL-label, such as Tris (2,2'-bipyridine) ruthenium (Ru) that is coupled to a detection probe (chemical, DNA, protein, and drugs), and a substance that is oxidized, such as tripropylamine (TPA), present in the reaction buffer. When an RF voltage is applied to an electrode, both components are activated by oxidation. The oxidized substance is transferred into a highly reducing agent, which reacts with activated ECL label to create an excited-state form. This form returns to its ground state with emission of a photon at wavelength at 620 nm and long excited state lifetime (~600 ns) at room temperature. The amount of light produced is directly proportional to the amount of ECL label bound on the IC chip of the present invention and can be captured by the light detection systems 11 (e.g. photo detector, camera, microscope . . . etc.). The production of light indicates the ECL conjugated target binds to the chip powered by RF. Several commercial ECL reader systems are available (e.g. NucleiSens Reader from Organon Teknika company; IGEN).

Figure 5:
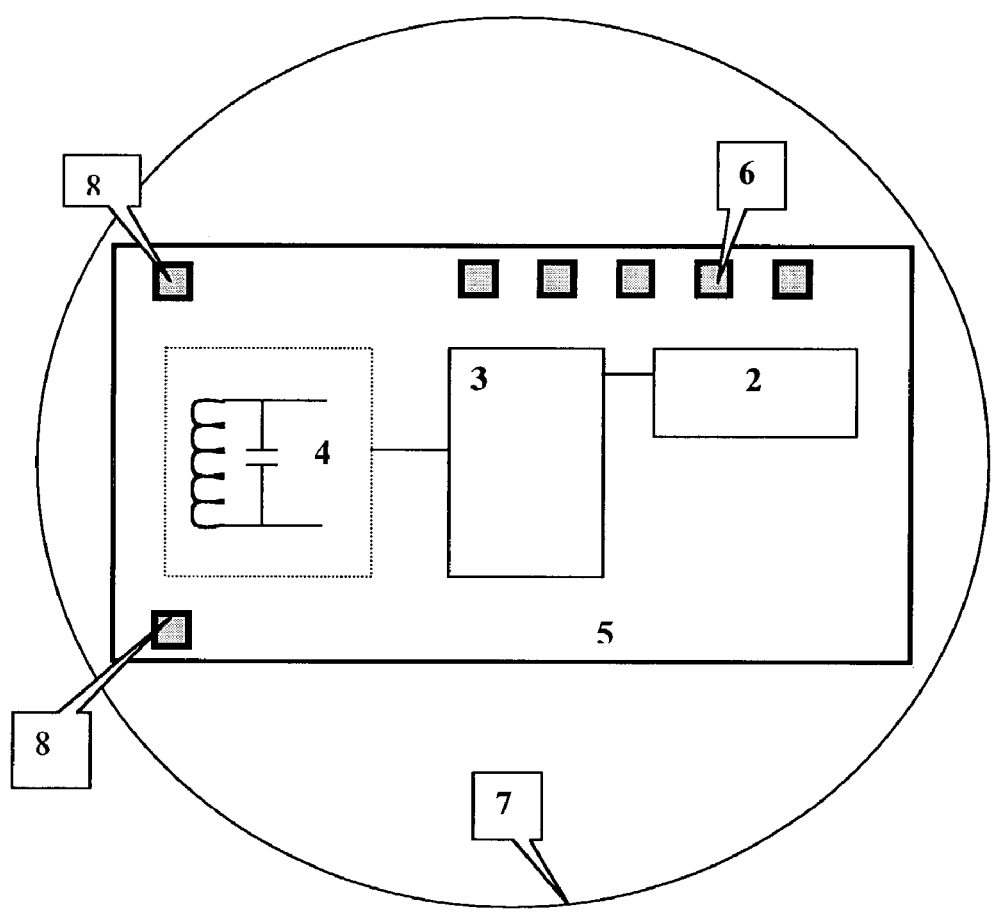
FIG. 5 shows RF system with electrode only and without metal option ID.
Figure 6:
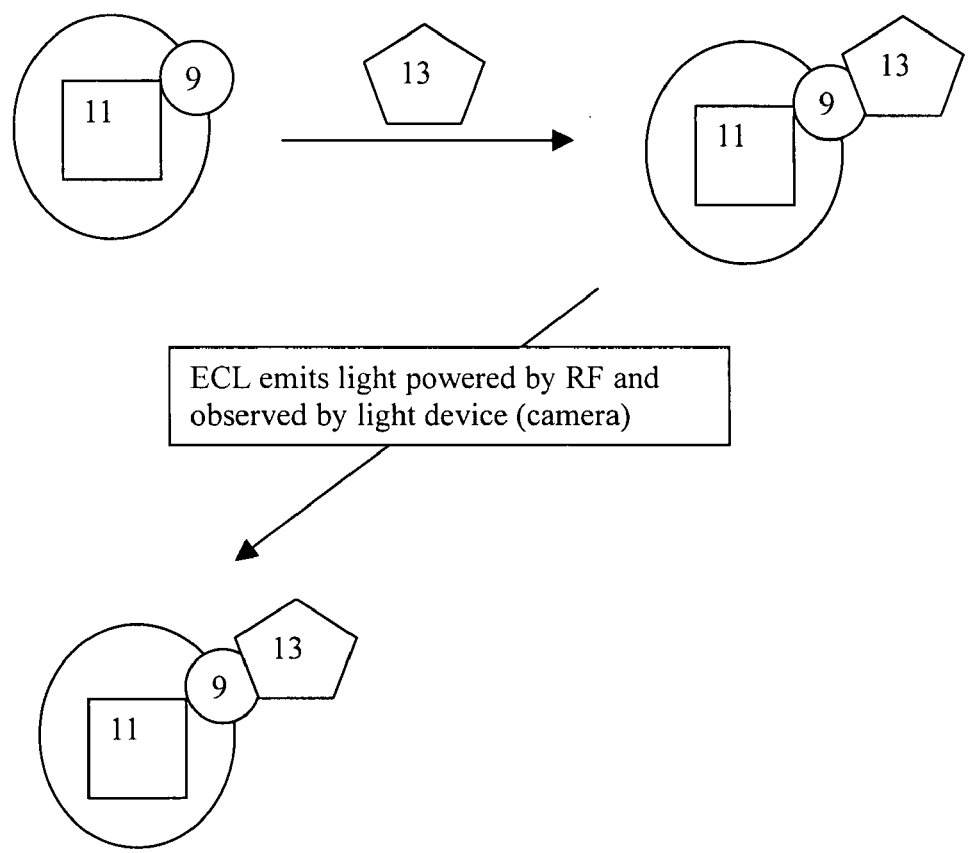
FIG. 6 depicts the procedure used with ECL labeled substance 13 with a chip only containing an electrode.

3) RF without metal ID function, but with ECL application only (FIGS. 5 and 6). FIG. 5 depicts the Vincogen chip without metal option ID. Modulator 2 makes the ID binary number to RF band. A Capacitor and Oscillator may also be inside the modulator. Analog font end 3 is an up-converter circuit basically to up-convert the binary ID to high frequency. The Antenna and Energy Gather Circuit 4 is used for receiving and sending the radiofrequency energy in and out the chip. Internal Block 5 and Pins 6 is used for testing or other reserved functions. It optionally contains a layer. $SiO_2$ protects most areas of IC and the I/O pins 6 and 8 area will expose to air. It can be added by the IC manufacture. Electrode 8 is the also the pins device. The pin device can provide very short time current for outside material. As shown in FIG. 6, the chip of the present invention will use the electricity (~3V) generated by RF to power the ECL conjugated target 13 when it binds to the substance 9 on the electrode present on the chip. The light will produce during the electrochemical reaction of ECL and electricity and capture by the light detective system (e.g. photo detector, camera, microscope . . . etc.). The light reaction indicates that the ECL conjugated target bound to the substance on the chip powered by RF.

In a specific embodiment, the IC chip of the present invention is a part of a system comprising a radio frequency identification system comprising: (i) an antenna which emits a radio signal; (ii) a transponder having a read-only tag, wherein said tag contains unique information and said transponder activated by said antenna of (i) and (iii) receiver which receives and decodes said information. In a specific embodiment, the information contains binary code.

Methods and Kits

The IC chip of the present invention can be used to detect the binding of a substance to a sample. In one embodiment, the IC chip of the present invention is contacted with a substance to determine whether this substance binds to the substance present on the IC chip. In one embodiment, the substance present on the IC chip contains a detectable moiety.

Figure 7:
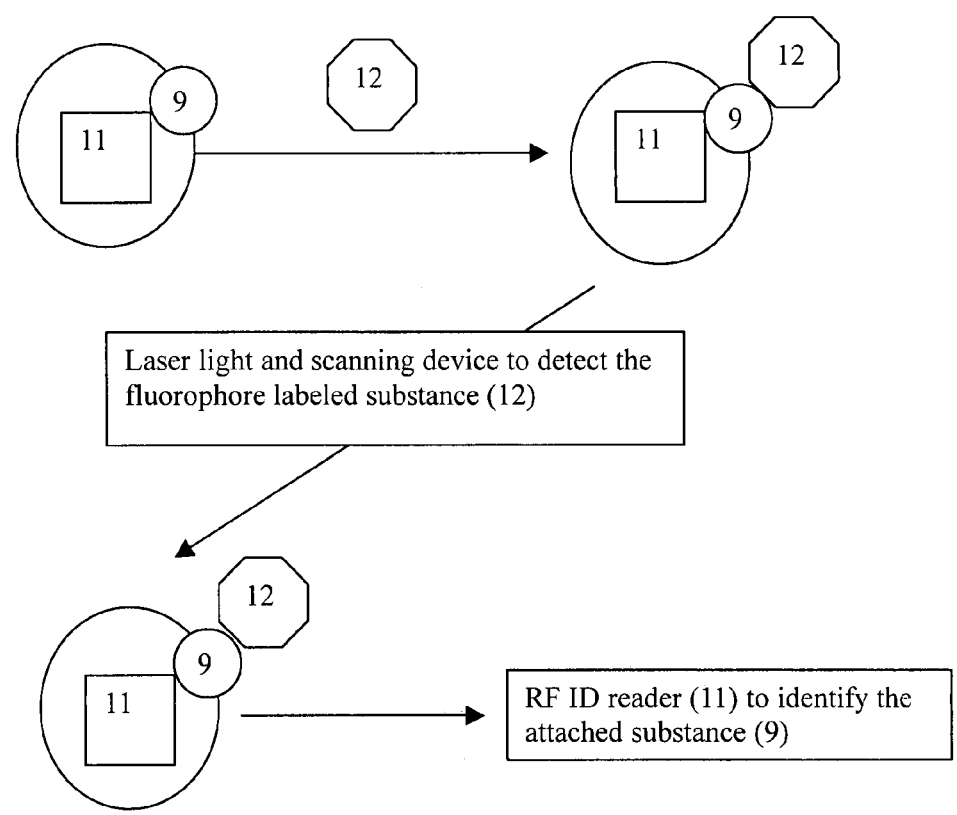
FIG. 7 shows use of fluorophore labeled substance with RFID chips.

In another embodiment, the substance that is contacted with the IC chip contains the detectable moiety (see FIG. 7). In a specific embodiment, the substance is a fluorophore labeled substance 12. A laser light and scanning device detects the fluorophore labeled substance and an RF ID reader 11 identifies the attached substance 9.

In yet another embodiment, the detectable moiety is added after the chip is contacted with the substance. For example, an IC chip may contain an antibody that is bound to a transponder. The antibody is incubated with antigen in, for example, a vessel, to obtain a reaction mixture. A second fluorescent or ECL-labeled antibody that binds to antigen is added to the mixture. The IC chips are then washed to remove any unbound components and reagents. The labeled antibody is detected with a fluorometer or ECL reader to identify those chips that have antigen bound. The bound unlabeled antibody can also be detected with BIA label-free, surface plasmon resonance (SPR) technology [Karlsson et al, (2000) 278, 1-13; BIACORE AB, Sweden]. These chips are decoded using a receiver.

Figure 8:
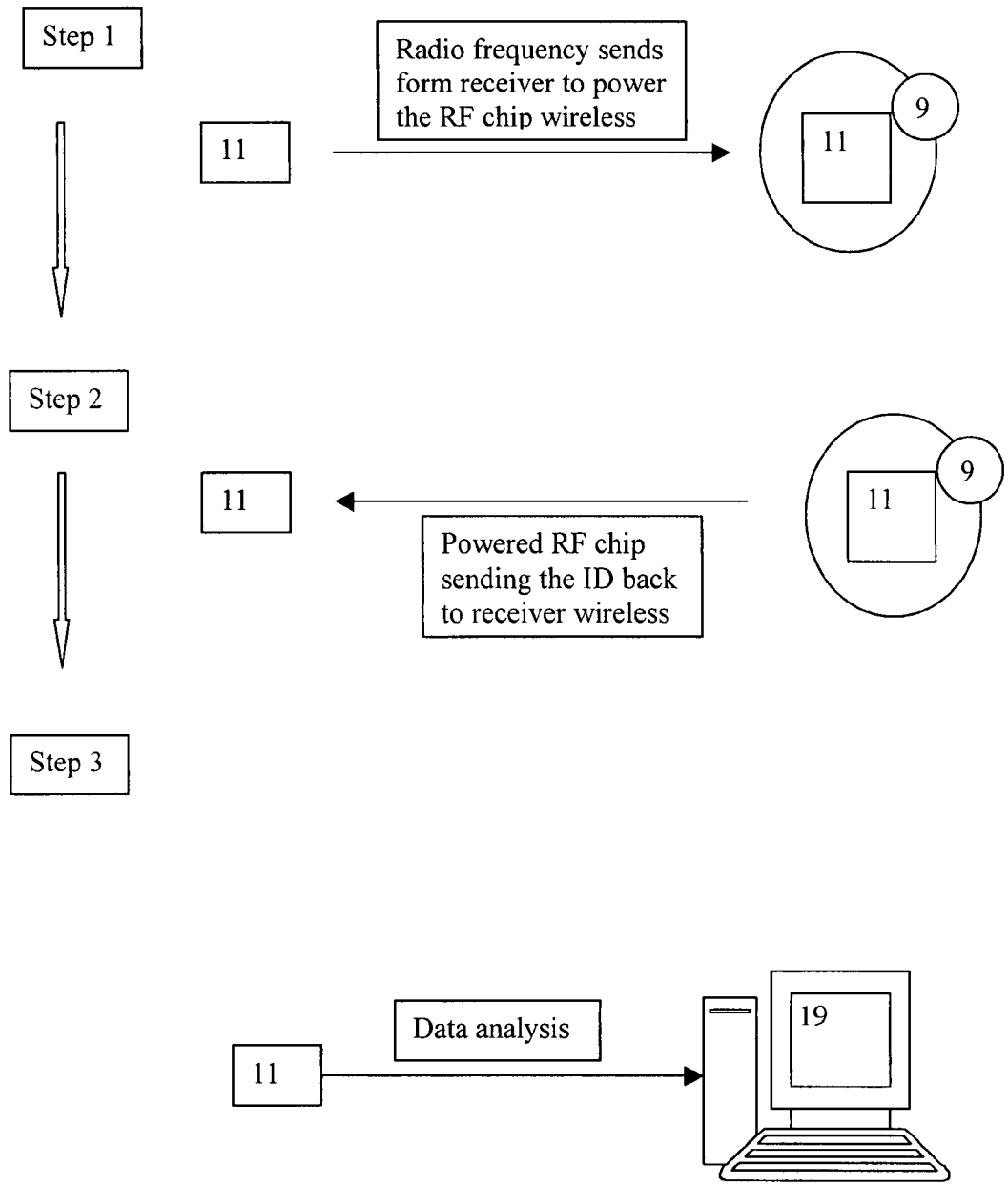
FIG. 8 shows the procedure used to generate and analyze information using the IC chips of the present invention.

A diagram of one embodiment of the present invention is shown in FIG. 8. The receiver 11 is a transceiver, which can transmit power to the RFID IC chip of the present invention through radiofrequency and receive ID from antenna and demodulate the ID from RF signal wireless. The ID can then send information to a PC or other postprocessing unit 19.

The assay of the present invention may, for example, be used to create the disease disorder protein profile in a patient's sample (blood, urine, saliva, sweat . . . etc.), and use it to diagnose a disorder. A sample from a patient may be screened with a panel of markers, for example, from a random peptide or antibody phage display chip library. The random peptide or antibody display library [Marks et al., (1991) J. Mol. Biol. 222, 581-597; Hoogenboom et al., (1992), J. Mol. Biol., 227, 381-388; Griffiths et al., (1993) EMBO J, 12, 725-734; Haard et al, (1999) J. Biol. Chem. 274, 18218-18230] may be created on T4 [Ren et al., (1996) Gene 195, 303-311; Ren et al., (1996) Protein Science 5, 1833-1843], M13 phage display system [Winter et al, (1994) Annu. Rev. Immunol, 12, 433-455; Clackson et al, (1994) Trends Biotechnol. 12, 173-184], or λ phage [Santini et al, (1998) 282, 125-135].

Figure 9:
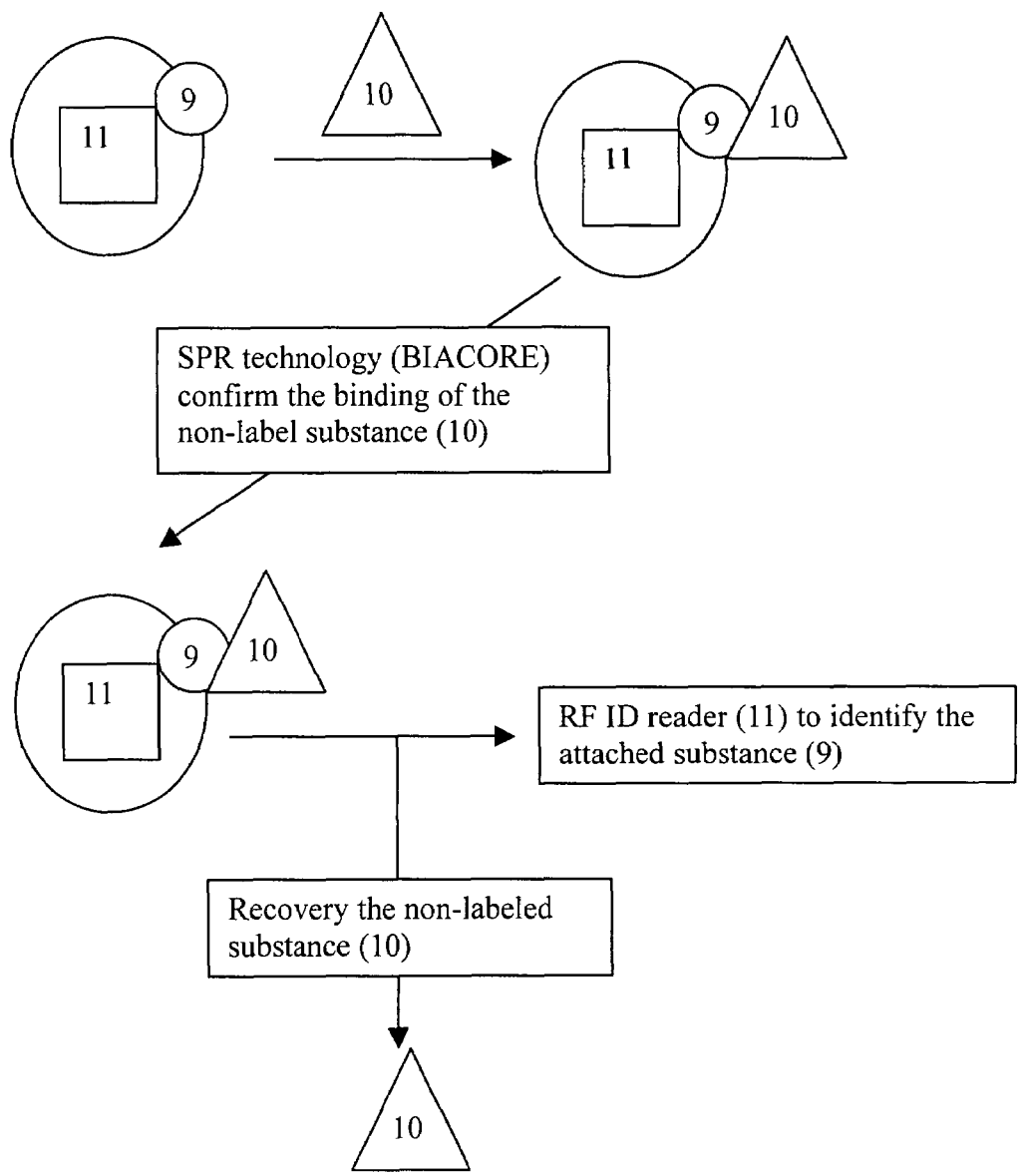
FIG. 9 shows the use of SPR technology with RFID chips.
Figure 10:
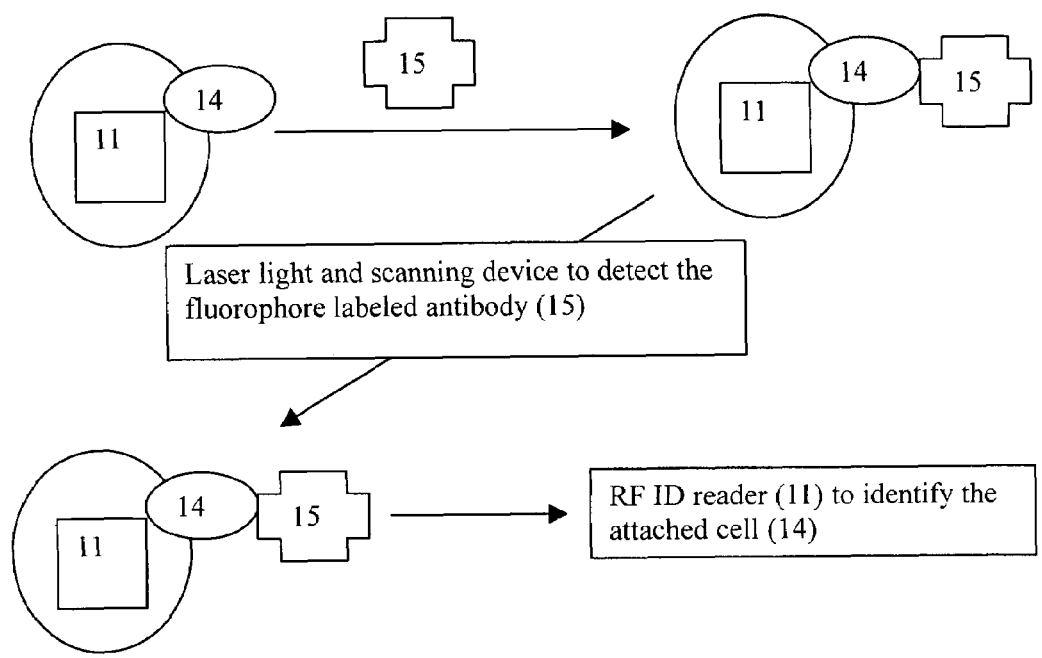
FIG. 10 shows the use of fluorophore labeled antibody with cell on RFID chip without the electrode.

As shown in FIG. 9, the antibody or random peptide (12-15 mer) phage display library can create more than $10^7$-$10^9$ individual clones enough to cover all possible epitopes. The random peptide or antibody IC chip display library 9 will screen the patient and normal person's serum 10. The patient will express several unique "disease associated proteins (antigens)" in the serum. Since the display library can cover $10^7$-$10^9$ individual epitopes, it should detect these unique "disease associated proteins (antigens)" in the serum to create the real profile and surrogate markers through binding of 9 and 10.

The primary screening procedure can be applied with a mixed IC chip library 9 containing different 1000 phage clones on each individual chip. A chip library containing $10^4$-$10^5$ chips for the first screening can be obtained from $10^7$-$10^9$ individual clones. The screening procedure involves the incubation of a chip library with the sample for a period of e.g., 1 hr. The unbound sample is washed away thoroughly with the washing buffer and the bound chip is identified with BIA label-free, surface plasmon resonance (SPR) technology [Karlsson et al, (2000) 278, 1-13; BIACORE AB, Sweden]. The binding status of the chip can be detected and confirmed by SPR directly. The reader 11 can identify the RF ID. This process may be repeated in the mixture IC chip library with only one clone on each individual chip to determine the real clone or chip that can interact with patient's serum only. All of the positive clones' IDs will form the "expression profile of surrogate markers" for this disease may be analyzed by PC or other post-processing unit. This profile can be used as a diagnosis for disease progression, the new drug targets, or for a vaccine.

A multiplex assay is conducted in a similar manner. Two or more IC chips of the present invention are placed in each assay vessel to detect two or more substances simultaneously. The IC chips are divided into two or more classes, with each class having a distinct index number.

The multiplex assay of the present invention may be used to 1) identify an unknown antagonist or agonist from phage display library on chip; 2) identify an unknown antagonist or agonist from monoclonal display library on chip; 3) identify an unknown antagonist or agonist from the gene-expression IC chip library; 4) identify the unknown antagonist or agonist from the gene-expression IC chip library using a mixture of substances (e.g. extract of Herbs). Assays of gene expression libraries will primarily focus on promoter regions.

The transponder used in the method of the present invention along with a nonradioactively labeled substance may be packaged as a kit. An example of such a substance is a labeled antibody. Alternatively, the kit of the present invention may comprise the transponder and a detectable moiety, such a luminescent moiety, an enzyme, such as alkaline phosphatase and substrate. The kit may further comprise a standard. The kit of the present invention may also comprise a standard compound Specific Embodiments The IC Chip is small and designed with radio reflect (RF) ID that can be used in high throughput drug screening, real-time live cells monitoring processes, and gene expression profiles with different materials (DNA, proteins, chemicals, and cells) on it. This small IC chip does not need power on itself because it gets power from radio signal and reflect the code from its metal option ID. It can be separated, and recovered by sorter. For example, with 14 bits it can generate $2^{14}=16384$ number to identify each individual chip. It is essential to identify each individual chip with these numbers to reveal the materials (DNA, protein, chemicals, cells) on it during the final recovery and decoding processes with radio reflect signal. The chip can be embedded into different shapes (e.g., bead, square) made of $SiO_2$.

Real-Time Live Cells Monitoring Process by IC Chip

A. One Cell Type:

1. Single Reagent Treatment:

Target cells (one cell type) are cultured or attached on the surface of transponders/chips (bead shape), and then are treated with reagent for designated period of time. The surface of the chip is treated with poly-L-lysine. The reagents include but are not limited to drugs, chemicals, biological substances (e.g., fluorescent protein, cytokines, endocrines), pathogens (e.g., virus), and toxins. During different time points, the chips are separated and recovered. The specific fluorescent reagents (e.g., fluorescent probe, fluorescent protein) are incubated with chips and the unbound fluorescent reagent is washed away. A cell sorter, reader, and multimode microscopy is used to measure the intensity and localization of fluorescence reagents for various biological processes occurring in live cells, such as the presence of cell surface antigens (e.g., MHC antigen, HIV gp120, . . . etc.), metabolic processes (e.g., changes in mitochondrial potential [Waggoner A. S. (1985) "Dye probes of cell, organelle, and vesicle membrane potentials" In The Enzymes of Biological Membranes, $2^{nd}$ Ed, Edited by Martonosi A. Plenum; pp. 313-331] or free metal ion concentration $H^+$ and $Ca^{2+}$ [Baazov et al, (1999) *Biochemistry* 38, 1435-1445; Grynkiweicz et al, (1985) *J. Biol. Chem.* 260, 3440-3450], membrane receptors (e.g., cytokine receptor, endocrine receptor number change), gene activity (e.g., transcription factors, translation factors, protein expression), cell cycle identification (e.g., G0, G1, M, S phases time curve) or to characterize such cellular components such as cellular organelles, cytoskeleton [Dailey et al., (1999) *Methods* 18, 222-230; Dai et al., (2000) *J. Cell Biol.* 150, 1321-1334].

This information provides the time curve of this biological process by specific biomarker. The recovered cell sample can also be used for further molecular analysis (e.g. PCR) or protein analysis (e.g. HPLC, GC/MS) by end-user.

2. Multiple Treatments:

Target cells (one cell type) are cultured on the surface of IC chips, then different RF ID of cultured cells are treated with different reagents or different treatments. For example, the HIV infected cells are on one ID chip and HIV naive cells are on different ID chips. Alternatively, different concentrations of HIV infected cells may be cultured on different chips; each chip has its own ID. All chips are cultured in the medium with or without reagents (e.g. drugs) and the gene expression of cellular proteins (e.g. chemokine receptor) and viral protein (e.g. HIV gp120) is monitored.

In a specific example, the HIV dynamic cycle in HIV secondary infected naïve cells is studied. Cell samples are taken every hour to measure the HIV gp160 on the cell surface for 24 hours. Every hour, the RF receiver chooses the chip to include all the different concentration or strains infected cells and naïve cells through their unique RF ID. The chosen chips are then analyzed by anti-HIV gp160 (or other studied target protein) antibody conjugated or with fluorescence probe. The antibody is incubated with chips for a period of time and washed thoroughly to remove the unbound antibody. The flurorescence reader is used to determine flurorescence intensity over a 24 hour period. The whole experiment provides a whole picture of the dynamic time curve of interaction of cell response as well as viral expression between different strains in the same condition.

B. Mixed Cell Types:

The chips can also be used to perform mixed cell type co-culture. This is very important to evaluate the cytokines, promoter, and cellular biological interactions between different cell types or treatments. The different cell types of cells are cultured on the surface of transponders with different RF ID, then treated with reagents. During different time points, the transponders are recovered and separated by cell sorter to measure fluorescence for the function, characteristic and/or marker to be assayed from the live cells. The different RF ID of cultured cells can then be decoded. The analysis gives the time curve of biological processes under co-cultured conditions.

1. HIV Infected Cells

Different kinds of HIV infected cells (e.g. macrophage tropism or lymphocytes tropism) may be treated with different concentrations of anti-HIV drugs or the different combination of anti-HIV drugs (cocktail treatment). In each treatment, the different kind of HIV infected cell will have a unique ID on the chip. The infected cell may be screened with anti-gp160 or other related antibody conjugated with fluorescence probe as described above.

It is suggested that there are reservoirs (infected cells) in HIV patient after anti-HIV "cocktail" drugs treatment. The cell types of these HIV reservoirs are still unclear, although the neural cell has been suggested. It is very important to identify these reservoirs and to find new treatments to eradicate HIV. By using the mixed cell IC chip culture, HIV susceptible cells can be identified through HIV antigens on the cell surface. Mixed cells on the chip are then treated with anti-HIV cocktail drugs or drug candidates to identify the efficacy and model system for HIV treatment.

Furthermore, an HIV biochip library can detect multi-HIV proteins (antigens) and other opportunistic pathogens' antigens in one assay. HIV proteins are Gag (p17, p24, p7), Protease (p15), Reverse Transcriptase (p66, p51), Integrase, Env (gp160, gp120, gp41), Tat (p16/p14), Rev (p19), Vif (p23), Vpr, Vpu, Nef, Tev. Basically, the HIV wild type proteins and mutants' proteins are being assembled in phage expression display library or by synthesis in vitro (*E. coli*, yeast, other eukaryotic cells). It will also include all possible mutants of HIV proteins in this display library. All proteins will be attached on the surface of RF chip to form chip library as described previously. The sample from the patient is incubated with the chip library for a time period to let human anti-HIV antibodies to bind to the viral protein on the chip. The unbound sample is thoroughly washed with washing buffer and removed from the chip. The $2^{nd}$ anti-human antibody conjugated with fluorescence will be added to incubate with chip for a time period. The unbound anti-human antibody conjugated with fluorescence will be removed by washing buffer again. A laser light and scanning device detects the fluorophore labeled antibody and an RFID reader. The SPR technology can also be applied here for without using $2^{nd}$ anti-human antibody conjugated with fluorescence.

Each protein is attached on the surface of individual IC chip to create the display IC chip HIV library for screening purpose. The HIV patient's sample may be screened with this display chip library once a week to monitor the change of the HIV population. This will help patient, physician, and medical system to save cost on HIV health care and also benefit the patient to change the new combination of anti-HIV drugs therapy as early as possible. Most of all, the information of HIV mutants dynamic profile through the drug treatment will let to predict the HIV mutants even before these HIV drugs treatment. Then we can use this information for vaccine and new drugs development. 2. Promoter Function It is very common to study the promoter function with fluorescent reporter genes on different cell lines by transfection the gene into the cell. Several transfection technologies available include DEAE-dextran, calcium phosphate, electroportation, cationic liposomes, retrovirus-mediated, biolistic particle, activated dendrimers, nonliposomal lipids, and microinjection [The Qiagen Transfection Resource Book, 1999]. Using conventional procedures, different cells are cultured in separate wells and treated with transfection mixture. It is a labor-intensive process and there is experimental data deviation due to human error on transfection mixture. With different cells on different chips, the experiment can be performed in the same condition with the same transfection mixture. Then analysis of the results could be performed with high throughput convenience.

Drug Screening Using IC Chips:

The toxicity and efficacy test of a drug candidate is a very important issue for the pharmaceutical industry. Right now, in vitro cell culture assay systems have several drawbacks. The serious one is that each cell needs to be cultured individually. In human or other higher organisms, all cells interact with each other via cytokine and endocrine system. In order to achieve the condition as close to natural physiological condition, mixed cells culture with the IC chip of the present invention could be performed.

The different target cells (primary cells or cell line) can be attached on different IC chips. Then all the cells can be treated or incubated with the drug candidate to observe the cytotoxicity in each cells under biological interaction conditions that mimic the real human physiological condition.

Each IC chip with a different target protein contains a unique signal or number generated by the embedded IC. For example, with 14 bit of metal option ID, $2^{14}$=16,384 kinds of IC Chips can be created to label different proteins or genes. This unique signal or ID can be used to identify which gene or protein is on the IC Chip. All proteins from human, bacteria, virus, and other microorganisms for potential drug targets can be expressed in vitro or phage display system and conjugated onto chips to create a drug-screening library. The drug-screening library can constitute 15,000 different kinds of proteins with different identification of IC chips in it. The sequence of the human Genome [Venter et al., (2001) Science 291, 1304-1351] has made the gene information available.

The gene expression IC chip libraries from different organisms (includes human, mouse, rat, pathogen, bacteria, virus) are constructed by protein expression technology or phage display system and each protein is attached to one single IC chip 9.

Substance (protein, antibody, ribozyme, toxin) without label or labeled by fluorescence directly, by fluorescence-conjugated antibody, or by different RF ID 17 (FIG. 12) is incubated with the drug-screening library for 2 hours at 4° C. The library is then washed with 3 times of washing buffer (e.g. BSA-detergents) to remove free substance. In RF ID probe system, the sample can be treated with protein cross-link reagents available commercially to create the covalent link between substance 9 and 17. Then reader 11 can determine both IDs.

The drug-screening library bound with fluorescence labeled substance is sorted and recovered by the sorter. The SPR technology will be used to screen and recover the chemical-bound chip if no-labeled substance is used. The recovered chips can be decoded through its specific embedded IC number and a specific protein can be identified. The bound substance also can be analyzed for its identity (e.g GC/MS, HPLC). The identified protein on the chip that can bind to drug will be the candidate for further analysis.

Screening *Ganoderma lucidum*

Medical mushrooms have been used in medicine societies and have been used as immunomodulators, anti-HIV and anti-tumor agents. One of the most useful medical mushrooms is *Ganoderma lucidum* that has been used as a remedy for longevity and health in Asia for thousands of years. Several isolated active compounds such as polysaccharides (β-glucan, hetero-β-glucan, acidic heteroglucan, chitin xyloglucan), minor minerals as well as small peptides have been identified [Tanaka et al., (1989) *J. Biol. Chem.* 264, 16372-16377; Willard, (1990) Reishi Mushroom. Issaquah, Sylvan Press, Vancouver, BC, Canada; Wasser and Weis, (1999) *Critical Reviews in Immunology* 19: 65-96]. Treatment of animals of pure mycelium and culture metabolites of *Ganoderma*, results in increased phagocytosis activity and numbers of liver Kupffer cells to remove the waste & necrotic tissues [Liu et al. (1988) *The Chinese Pharm. J.* 40, 21-29]. Results of in vitro studies of macrophages and T-lymphocytes indicate that the secretions of cytokines (IL-1, IL-6, TNF-α, and IFN-γ) are enhanced by *Ganoderma lucidum* [Wang et al., (1997) *Int. J. Cancer* 70, 699-705]. In clinical studies, the liver function of patients with chronic hepatitis B and acute exacerbation can be recovered due to the regeneration of hepatocytes by *Ganoderma* [Phounsavan, Say Fone, (1991) *The 5th international conference on immunopharmacology*, Tampa, Fla., USA. Abstracts, p. 52].

Gene expression IC chip libraries from humans are used to screen the *Ganoderma* extract. The screening procedure is similar to those given above. Briefly, the *Ganoderma* extract is incubated with the human gene expression RF IC chip libraries for a period of time to let *Ganoderma* ingredients bind to the human gene expression RF IC chip library. The bound chips can be detected by SPR technology due to unlabeled probe. The specific gene can be identified through its unique RF ID immediately. The bound ingredients from *Ganoderma* can be analyzed and purified later as a new drug candidate.

Determining Ingredients in Herbs

Right now there is no method or standard to determine the effective ingredients in herbs. This is due to the extreme complexity of ingredients that include polysaccharides, minor minerals and proteins. A phage display chip library is used to set up the ingredient profile of target herbs. This profile of ingredients of Herbs serves as an index to certify the efficacy of herbs. With this index profile, government, consumers, merchants will have a standard to judge the ingredients of the Herbs.

Briefly, the antibody or random peptide (12-15 mer) phage display library can create more than $10^7$-$10^9$ individual clones enough to cover all possible binding possibility to all ingredients in herbs. The primary screening procedure will be applied to the IC chip library with 1000 different phage clones on each individual chip. A chip library containing $10^4$-$10^5$ chips for the first screening can be obtained from $10^7$-$10^9$ individual clones. The screening procedure is the incubation of chip library with sample for a period (1 hr). The unbound sample is washed away with the washing buffer thoroughly and identify the bound chip is identified with BIA label-free, surface plasmon resonance (SPR) technology [BIACORE AB, Sweden]. The binding status of the chip can be detected and confirmed by SPR directly. This process will be repeated in the mixed IC chip library with only one clone on each individual chip to determine the real clone or chip that can interact with patient's serum only. The combination of the positive ID of bound chips will be the index profile of the herbs in this case.

Most of all, the antibody display library from the positive chip can be used to make the antibody affinity column to purify the specific ingredients.

Detection of Pathogens

Figure 11:
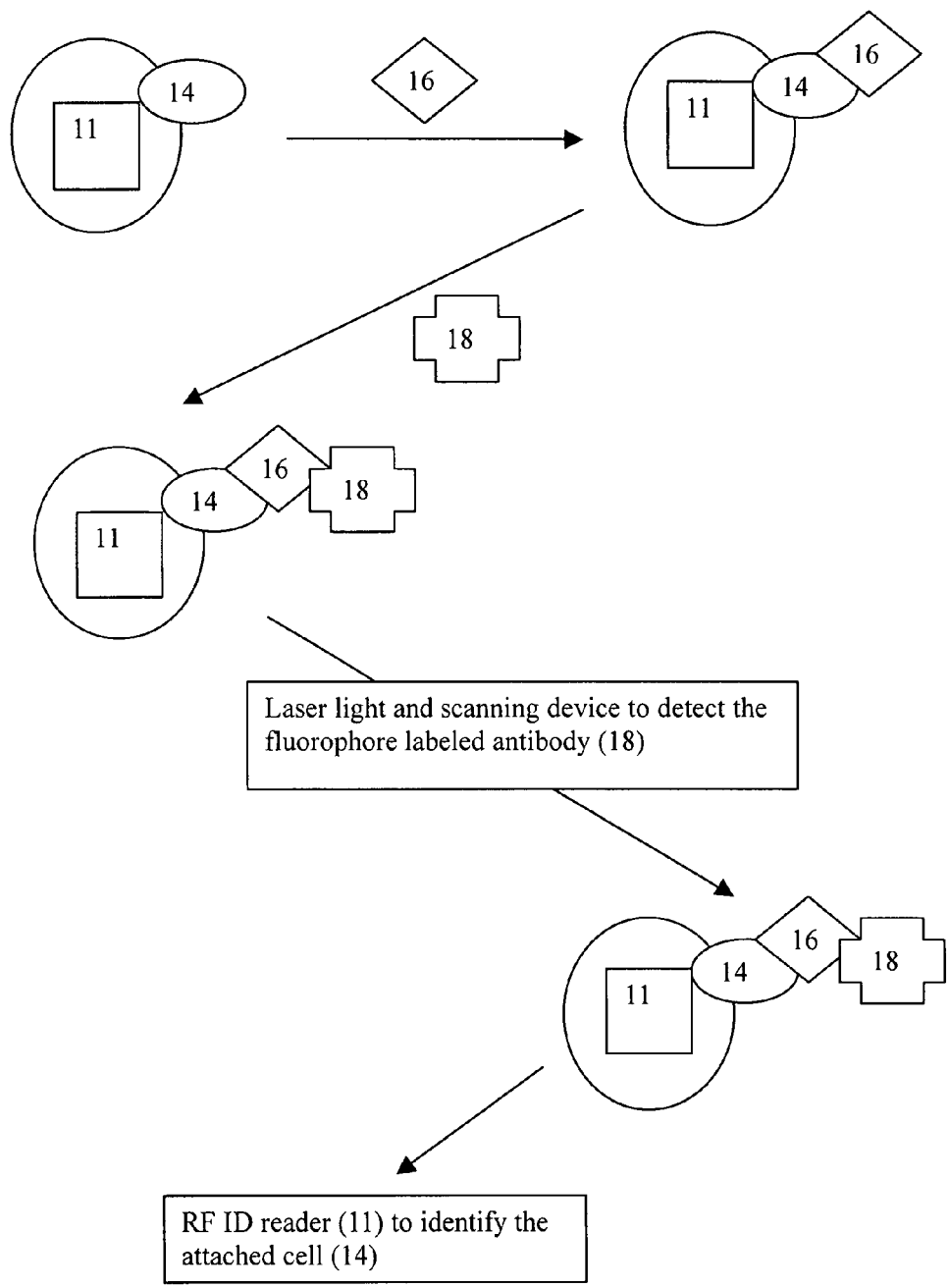
FIG. 11 shows a specific embodiment where the primary antibody is nonlabeled.
Figure 12:
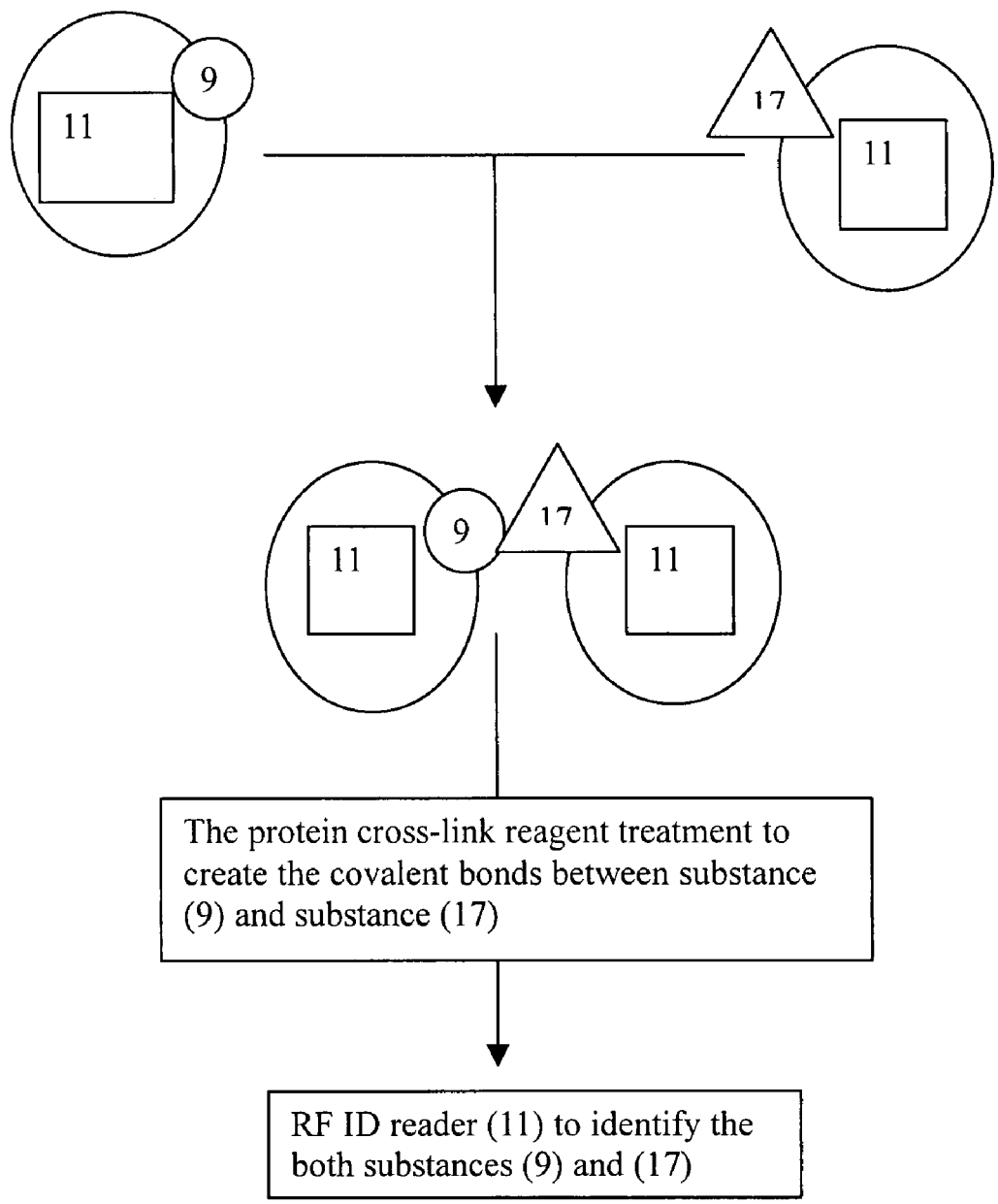
FIG. 12 shows RF ID probe system.

Lymphoid (hemocytes), gill cells from pregnant black tiger shrimp (*Penaeus monodon*) may be assayed to detect the presence of pathogens [Vargas et al, (1998) Advances in Shrimp biotechnology, $5^{th}$ Asian Fisheries Forum, pp 161-167]. There are more than 14 viral pathogens to infect the black tiger shrimp. The most serious viral pathogen is White Spot Syndrome Virus (WSSV) (Gene Bank #NC_003225). The presence of the pathogen's antigen on cell surface is detected using an antibody to the pathogen's specific antigen. Diagrams of general procedures used are depicted in FIGS. 11 and 12. The cells 14 are attached and cultured on the IC chips used in the method of the present invention. Each chip with unique ID only attaches one shrimp's cells 14. These cells on the chip are incubated with fixing solution (e.g. tetraformaaldehyde, ethanol) to fix all the proteins on the cell membrane first. Then it is contacted with antibody against the pathogen's specific antigen. The antibody is labeled 16 or alternatively, the mixture is incubated with a secondary labeled antibody 18 bound to the primary antibody 16. The chips are washed with washing buffer to remove unbound antibody and scanned for fluorescence-positive chips to identify infection of the virus in shrimp. The advantage of chip technology is that over 20,000 shrimp samples can be checked within 2 days with low cost than any conventional methods.

The specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

Various references are cited herein, the disclosures of which are incorporated by reference in their entireties.

What is claimed is:

1. An integrated circuit chip for use in an assay of a substance comprising:
   a. a non-memory containing transponder having a metal option and read-only tag containing an index ID created by a photomask process, wherein said index ID is transmitted to a receiver in response to a radio signal:
   b. at least one substance attached to said transponder, wherein said substance is selected from the group consisting of a biological molecule, hormone, pharmacological agent, tranquilizer, barbiturate, alkaloid, steroid, vitamin, amino acid, sugar, biotin, aviden and streptavidin; and
   c. an antenna for receiving and emitting radio signal.

2. The chip according to claim 1, wherein the substance is covalently attached to said transponder.

3. The chip according to claim 1, wherein the substance is noncovalently attached to said transponder.

4. The chip according to claim 1, wherein the substance is a biological molecule.

5. The chip according to claim 4, wherein the biological molecule is selected from the group consisting of a nucleic acid, protein, antibody and at least one cell or subcellular component thereof.

6. The chip according to claim 4, wherein said biological molecule is a member of a phage display library.

7. The chip according to claim 4, wherein said biological molecule is a cell comprising a pathogen.

8. The chip according to claim 1, wherein said substance comprises a detectable moiety.

9. The chip according to claim 1, wherein said transponder comprises binary code.

10. The chip according to claim 1, wherein said transponder further comprises an electrode and said substance is contacted with said electrode.

11. The chip according to claim 1, wherein said substance is contacted with an electrode.

12. The system according to claim 1, wherein said antenna is attached to said transponder.

13. A method for detecting binding of a first substance to a second substance comprising
   a. incubating the integrated chip of claim 1, the substance attached to said transponder is a first substance, with a second substance for a time and under conditions for the first and second substances to bind;
   b. analyzing the incubated mixture of step a to detect binding of said first substance and said second substance and
   c. identifying the substance attached to said transponder.

14. The method according to claim 13, wherein the substance attached to said transponder is identified by decoding information on said transponder.

15. The method according to claim 13, wherein said substance attached to said transponder is a biological sample.

16. The method according to claim 15, wherein said biological sample is selected from the group consisting of a cell, subcellular component, virus and tissue.

17. The method according to claim 13, wherein said substance attached to said transponder is a substance comprising a detectable moiety.

18. The method according to claim 13, wherein said substance attached to said transponder is selected from the group consisting of DNA, RNA, protein, natural product and pharmacological agent.

19. The method according to claim 13, wherein said substance attached to said transponder is an antibody.

20. The method according to claim 19, wherein said antibody is a monoclonal antibody.

21. The method according to claim 13, wherein said substance attached to said transponder is a fusion protein.

22. The method according to claim 13, wherein said substance attached to said transponder is a member of a display library.

23. The method according to claim 13, wherein said substance attached to said transponder is a member of a phage display library.

24. The method according to claim 23, wherein said library is selected from the group consisting of a gene expression library, protein library and antibody library.

25. The method according to claim 17, wherein said substance attached to said transponder is a ligand.

26. The method according to claim 17, wherein said detectable moiety is selected from the group consisting of a chromophore, fluorophore and luminescent agent.

27. The method according to claim 17 wherein said detectable moiety is a luminescent agent selected from the group consisting of a chemiluminescent, photoluminescent, bioluminescent and electrochemiluminescent agent.

28. The method according to claim 13, wherein said transponder further comprises an electrode.

29. The method according to claim 28, wherein said substance is attached to said electrode.

30. The method according to claim 29, wherein said substance attached to said electrode is contacted with a substance having an electrochemiluminescent moiety.

31. The method according to claim 29, wherein said substance attached to said electrode is contacted with a substance containing an electrochemiluminescent moiety.

32. The method according to claim 17, wherein said substance comprising a detectable moiety is selected from the group consisting of an antibody, a protein and a drug.

33. The method according to claim 13, wherein said substance attached to said transponder is a receptor.

34. The method according to claim 13, wherein said substance attached to said transponder is a ligand.

35. The method according to claim 13, wherein said second substance binding to said substance attached to said transponder is a biological sample.

36. The method according to claim 35, wherein said biological sample is selected from the group consisting of a blood, serum, saliva, urine, tissue, and cell sample.

37. The method according to claim 13, wherein said substance attached to said transponder is identified with SPR technology.

38. The method according to claim 13, wherein a detectable moiety is added to the mixture of step (a) before analyzing said mixture.

39. A method for detecting binding of a biological molecule to a substance comprising
   a. incubating the integrated chip of claim 1, wherein said substance attached to said transponder on said chip is a biologicaal molecule, with a substance labeled with a detectable moiety;
   b. analyzing the incubated mixture of step a to detect binding of said biological molecule to said labeled substance and
   c. identifying the biological molecule attached to said transponder.

40. A method for detecting binding of a biological molecule to a substance comprising
   a. incubating the integrated circuit chip of claim 1, said substance to said transponder on said chip having a detectable moiety, with a biological molecule;
   b. analyzing the incubated mixture of step a to detect binding of said biological molecule to said substance attached to said transponder and
   c. identifying the biological molecule attached to said transponder.

41. The method according to claim 39 or claim 40 wherein said biological molecule is a biological sample.

42. The method according to claim 41, wherein said biological sample is selected from the group consisting of tissue, one or more cells, virus particles and subcellular structures.

43. The method according to claim 41, wherein the labeled substance is a pharmacological agent.

44. The method according to claim 41, wherein said detectable moiety is added to the mixture of step a before analyzing said mixture.

45. A method for obtaining the integrated circuit chip of claim 1, comprising attaching a substance to a transponder containing a tag specific to said transponder, said tag containing information which identifies said transponder and is identified by (i) activating said tag with radiowaves and (ii) decoding said information on said tag.

46. The method according to claim 45, wherein the attachment of said biological molecule to said transponder is facilitated with a conjugating agent.

47. The method according to claim 45, wherein said method further comprises contacting said substance with a detectable moiety.

48. A multiplex assay method comprising:
   a. providing multiple integrated circuit chips of claim 1 which comprise one or more substances attached to said chips;
   b. contacting said chips with one or more substances to determine if said substance binds to a substance on each of said chips;
   c. analyzing the incubated mixture of step b to detect binding of said substance to said chips and
   d. identifying the substances bound to said substance on said chips.

49. The method according to claim 48, wherein each integrated circuit chip comprises the same substance.

50. The method according to claim 48, wherein said substance on each chip is a biological sample.

51. The method according to claim 48, wherein said substance on one or more chips comprises a detectable moiety.

52. The method according to claim 48, wherein each chip is contacted with more than one substance containing a detectable moiety.

53. The method according to claim 48, wherein each chip comprises the same biological molecule and each chip is contacted with more than one substance.

54. The method according to claim 48 wherein each chip comprises the same substance and each chip is contacted with one or more biological samples.

55. The method according to claim 48, which further comprises adding a detectable moiety to the mixture of step a.

56. The method according to claim 48, which further comprises after step (b) and before step (c) separating the chips from one another.

57. A kit for assaying a biological molecule comprising the integrated circuit chip of claim 1.

58. The kit of claim 57, which further comprises a library of substances.

59. The kit according to claim 58, wherein the library is a phage display library.

60. The kit according to claim 57, which further comprises a detectable moiety.

* * * * *